United States Patent [19]
Cattani

[11] Patent Number: 5,330,641
[45] Date of Patent: Jul. 19, 1994

[54] SEPARATOR OF SOLID PARTICLES FOR VARIABLE DISCHARGE FLUID FLOW RATES IN DENTAL APPARATUS

[75] Inventor: Ennio Cattani, Parma, Italy
[73] Assignee: Cattani S.p.A., Parma, Italy
[21] Appl. No.: 12,318
[22] Filed: Feb. 2, 1993
[30] Foreign Application Priority Data
Feb. 19, 1992 [IT] Italy .............. M92A000025
[51] Int. Cl.⁵ .............. B01D 19/00; B01D 21/26; B01D 33/15
[52] U.S. Cl. .............. 210/188; 210/218; 210/512.1; 210/512.3; 96/158; 96/168; 96/195; 96/208; 433/92
[58] Field of Search .............. 210/188, 218, 512.1, 210/512.3, 787; 433/92; 96/157, 158, 167, 168, 195, 208; 209/144, 211

[56] References Cited
U.S. PATENT DOCUMENTS

| 487,056 | 11/1992 | Ohlsson | 494/44 |
| 1,328,835 | 1/1990 | Kasley | 415/203 |
| 1,933,119 | 10/1933 | Peltzer et al. | 494/37 |
| 2,429,978 | 11/1947 | Blanchard | 415/203 |
| 3,613,988 | 10/1971 | Tapp et al. | 494/44 |
| 4,067,494 | 1/1978 | Willus et al. | 494/43 |
| 4,360,428 | 11/1982 | Comparetto et al. | 433/92 |
| 4,772,255 | 9/1988 | Csillag et al. | 494/37 |
| 4,842,478 | 6/1981 | Durr et al. | 433/92 |
| 4,932,933 | 6/1990 | Becker et al. | 494/62 |
| 5,018,971 | 5/1991 | Trawöger et al. | 433/92 |

FOREIGN PATENT DOCUMENTS
0425451A3  5/1991  European Pat. Off.

*Primary Examiner*—Robert A. Dawson
*Assistant Examiner*—David Reitsnyder
*Attorney, Agent, or Firm*—Darby & Darby

[57] ABSTRACT

The invention relates to a separator of solid particles for variable flow rates of discharge from dental apparatus. The separator includes a container (3) equipped with an upper cylindrical zone (3a), having an inlet hole (5) for the fluid to be separated, in which rotates the rotor (2) of a centrifugal pump which initializes the separation of the particles by centrifugation; it further includes a truncoconical zone (3b) which, functioning as a cyclone, continues the separation of the solid particles and expels the fluid, freed of the particles, from the container (3).

4 Claims, 2 Drawing Sheets

SEPARATOR OF SOLID PARTICLES FOR VARIABLE DISCHARGE FLUID FLOW RATES IN DENTAL APPARATUS

BACKGROUND OF THE INVENTION

The invention relates to a separator of solid particles for variable discharge fluid flow rates in dental apparatus.

In dental apparatus there is a production of fluids containing water, blood, amalgam, chemical products, etc., which must be discharged to the sewers respecting the anti-pollution laws which state that certain substances, such as amalgam and the like may not be so discharged.

In particular, in dental apparatus that uses liquid ring pumps to aspirate fluid from the mouth of the patient, the production of polluting fluids that contain air, various liquids and heavy particles, is quite abundant if discontinuous. Before being discharged into the sewers, these fluids must be freed of the above-mentioned polluting fluids.

In order to effect the separation of the solid particles from the said fluids, various systems are presently in use such as for example decanting systems which employ syphons, filtering systems and centrifuge systems.

Each of these systems presents some drawbacks. Filtering systems, for example, require very frequent maintenance due to the need for filter substitution; sedimentation systems are not able to deal with large quantities of fluid and do not offer, in particular for elevated quantities of fluids, a sufficient degree of separation within acceptable times. Centrifuge systems require rather expensive and delicate apparatus, whose cost and constructional complications increase considerably when the fluid flow rates to be dealt with are high.

SUMMARY OF THE INVENTION

An aim of the present invention is to optimise the solid-particle separation devices, in particular for apparatus with discontinuous fluid production, by providing a separator that needs little maintenance, which is able to discharge variable quantities of fluid in a relatively short time and which provides a very high degree of separation, even in the case of small-dimension particles, over a large range of different discharge fluid flow rates.

These aims and advantages and more besides will all be attained by the invention, as it is characterised in the claims that follow, which comprises a container equipped with a cylindrical zone, equipped with an inlet hole for the fluid to be separated, in which cylindrical zone the rotor of a centrifuge pump rotates, which rotor initialises the separation of the particles by centrifugation; the invention further comprises a truncoconical zone which, opening a discharge hole in the container, functions as a cyclone in such a way as to continue the separation of the solid particles and cause the expulsion of the fluid, by now freed of the particles, from the container.

BRIEF DESCRIPTION OF THE DRAWINGS

Further characteristics and advantages of the present invention will better emerge from the detailed description that follows, together with the accompanying drawings which represent a preferred but not exclusive embodiment and in which.

DESCRIPTION OF THE PREFERRED EMBODIMENTS

Figure 1:
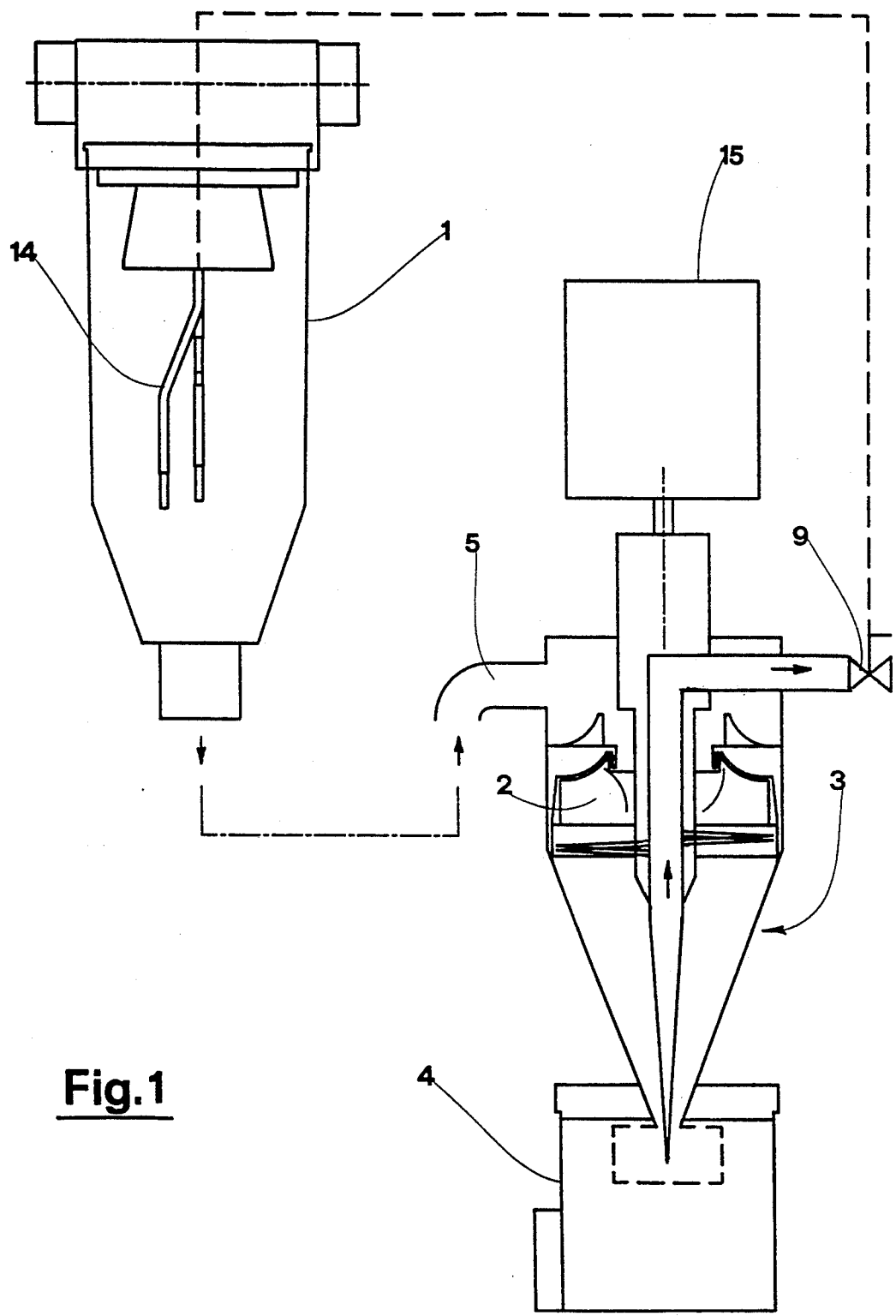
FIG. 1 shows a schematic view in vertical elevation of the various parts of the separator.
Figure 2:
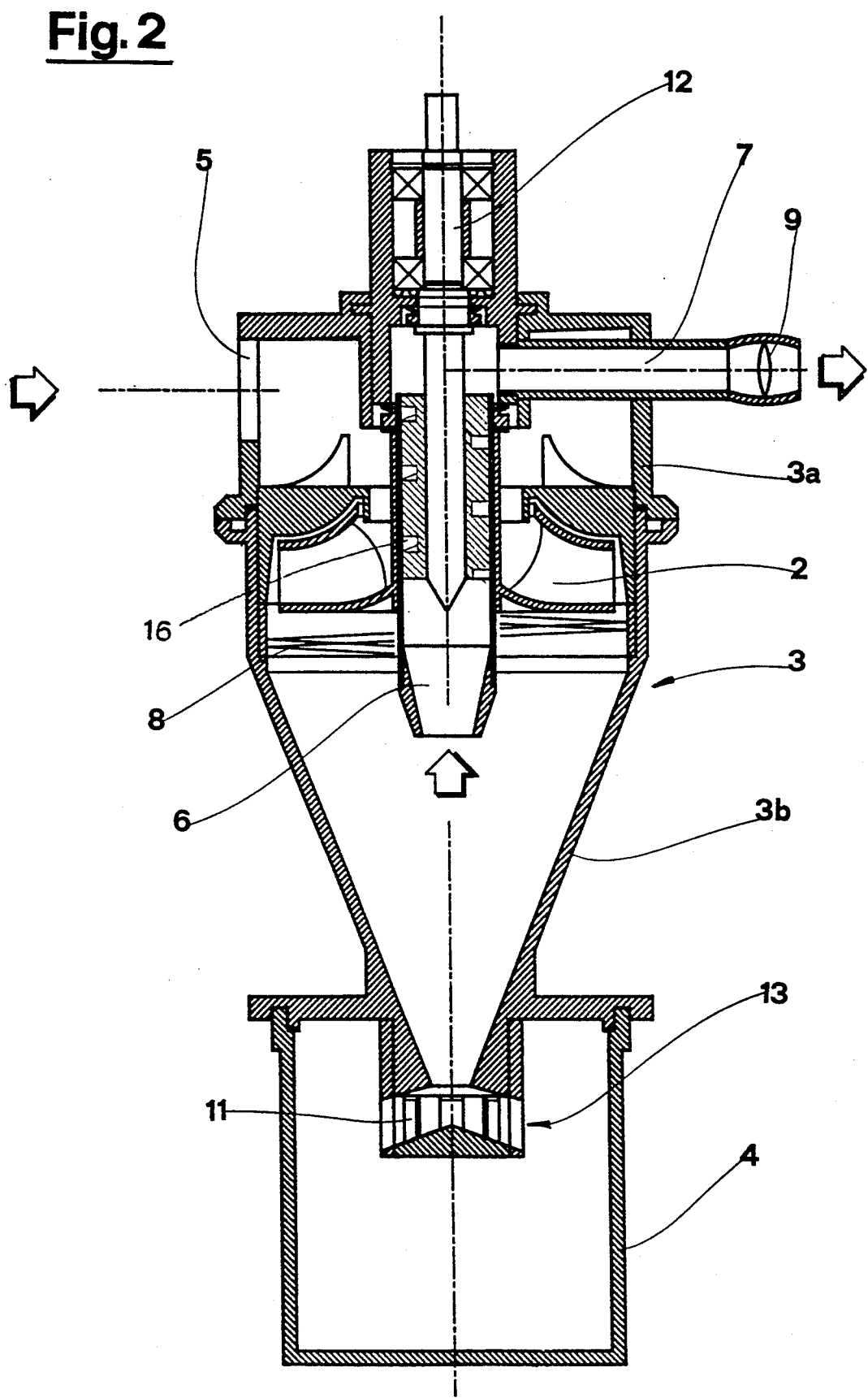
FIG. 2 shows a section, in vertical elevation and in enlarged scale, of the container of the separator.

The separator object of the invention comprises a separator chamber 1 which receives the fluids produced by a dental apparatus (not illustrated); these fluids comprise a gaseous part, generally air, a liquid part, generally water and other liquids used by the dental apparatus, as well as a solid part represented by solid particles, in particular by amalgam used for dental operations. In the separator chamber 1 the gaseous part of the fluid is separated from the remaining part of the fluid and exists upwards; the remaining part of the fluid collects in the chamber 1. In FIG. 1 the separator chamber 1 is shown as a separate element; the said separator chamber 1 could however form a single body with the remaining parts of the separator since its function is principally that of creating a water ahead and controlling its level.

Internally to the chamber 1 a probe system 14 is provided, of known type, which reads the level of the liquids inside the separator chamber 1 and provides command signals in relation to the levels recorded, of which more will be said hereinafter. The separator further comprises a container 3 equipped with an inlet hole 5 connected to the separator chamber 1; through the inlet hole 5 the container 3 freely receives the fluid from the separator chamber 1. In cases where the separator chamber 1 is at a lower level than the container 3, the passage of the fluid from the separator chamber 1 to the container 3 will be forced.

A collector 4 is provided on the bottom of the container 3, in which collector 4 the solid particles deposit; in the upper part of the container 3 an upper outlet hole 7 is provided, from which the liquids exit to the sewers once they have been cleaned of the solid particles. The container 3 comprises an upper cylindrical zone 3a wherein the inlet hole 5 is bored.

In the upper cylindrical zone 3a is the rotor 2 of a centrifugal pump whose inlet is connected to the inlet hole 5 in such a way that the fluid entering the container 3 all passes through the centrifugal pump itself. The rotor 2 is solid in rotation with a shaft 12 set in rotation by means of an electric motor 15. The upper cylindrical zone 3a does not communicate with the upper outlet hole 7 if not by means of the rotor 2.

The container 3 further comprises a lower truncoconical zone 3b which larger base is directly and freely connected to the upper cylindrical zone 3a and which smaller base opens into the collector 4.

A stop 13 is solidly connected to the smaller base of the lower truncoconical zone 3b, which stop 13 is contained in the collector 4; slits 11 are cut into the stop 13 and develop in an axial direction, placing the truncoconical zone in communication with the collector 4.

A spiral 8 is envisaged on the internal wall of the upper cylindrical zone 3a, which spiral 8 is arranged to be underlying the rotor 2 of the pump and terminates in proximity to the connection zone between the cylindrical and truncoconical zones of the container 3.

Also envisaged is a conduit 6, one of which ends is arranged axially to the truncoconical zone and in proximity to the larger base of the said zone, and which other end is connected with the upper outlet hole 7. The conduit 6 is bored internally to the hollow shaft 12.

One or more spiral channels 16 are made in the cavity of the shaft 12 for the passage of the fluid.

A. tap 9 is arranged on the upper outlet hole 7 which tap 9 opening and closing are commanded by the signals generated by the probe system 14. The functioning of the separator happens in the following way.

The fluid, constituted by air, liquid and solid particles, coming from the dental apparatus, enters the separator chamber 1; the air, and in general all of the gaseous parts, are separated and exit from the top of the separator chamber 1 while the liquid part with the solid particles suspended in it descends towards the lower part of the separator chamber 1 and passes freely into the container 3, in which container 3 the rotor 2 is continually in rotation and the tap 9 is normally closed.

The fluid entering into the container 3 passes through the rotor 2 of the pump and is centrifuged by it; in this way the solid particles are thrown towards the walls of the container 3 and, descending along the said walls, are conveyed into the collector 4.

The tap 9 being closed, the container 3 fills completely with fluid. Thanks to the action of the rotor 2, the fluid in the container assumes a rotary motion about the rotor axis; in this way the separation of the solid particles continues, and they are centrifuged and pushed towards the walls of the container 3, where they slide towards the collector 4.

When the probe system 14 shows that a certain predetermined level of fluid has reached the separator chamber 1 (that is, the separator), a command signal is generated which causes the tap 9 to be opened, thus permitting the discharge of the liquid from the conduit 6.

The fluid exiting from the rotor 2 crosses the spiral 8 which generates a downwards push and favours the creation of a primary vortex within the lower truncoconical zone 3b; at the smaller base of the lower truncoconical zone 3b a secondary vortex is established which rises upwards and permits the discharge of the water through the upper outlet hole 7. The vortex motion of the exiting fluid is favoured by the presence of the spiral channels 16.

In substance, by opening the tap 9, the lower truncoconical zone 3b behaves like a cyclone separator; also in the cyclone the solid particles are centrifuged against the walls of the container and descend towards the collector 4.

It should be noted that any eventual solid particles being transported upwards by the secondary vortex are centrifuged and returned downwards by the primary vortex.

When the level of the fluid in the separator chamber 1 falls below a second predetermined level, a further command signal is generated which causes the tap 9 to close; the motion of the fluid, towards the outlet, is interrupted, as is the secondary vortex of the cyclone; the fluid in the container 3 only maintains its rotary movement about the rotor 2 axis.

Apart from a brief initial transistory stage, the separator functions with the container 3 always full of fluid. The rotor 2 thus always rotates immersed in fluid and has the sole function of causing the rotary motion of the fluid contained in the container; this function is not influenced by the flow rate of the fluid and the rotor 2 can thus be very small in construction and have large inlets and outlets which do not tend to block.

When, following the opening of the tap 9, the cyclonic vortices are created, the normal drawbacks occurring in cyclonic separators and due to variations in flow rate do not arise, since given that the container 3 is always full, there are in fact no flow rate variations. It should also be noted that the rotary motion of the fluid is always initially caused by the rotor 2.

The separator behaves as a centrifugal separator, without discharge, when the tap 9 is closed, while it behaves as a cyclone separator, with constant flow rate, when the tap 9 is open. Also worthy of note is the fact that the cyclone treats fluid which is already at least partially freed of solid particles, which have been separated by centrifugal effect, to an extent depending on the time during which the separator has functioned solely as a centrifugal separator.

The slits 11 of the stop 13 almost completely deaden the turbulence of the fluid which enters the collector 4, and the same slits 11 prevent solid particles from being drawn upwards by the said turbulence and returned to the container 3.

Once the collector 4 contains a predetermined quantity of solid particles, the functioning of the separator is stopped and the separator is emptied of the fluid still contained in it; in these conditions the collector 4 can be disconnected and emptied.

What is claimed is:

1. A separator of liquids and solid particles from discharge material from a dental apparatus, comprising:
    a separator chamber, in which gases are removed from said discharge material;
    a container having an inlet hole, an upper section and a lower section, said container receiving said discharge material from said separator chamber through said inlet hole, said container also having an outlet hole, liquids separated from said discharge material being discharged through said outlet hole, said upper section being generally cylindrical, said inlet hole being in said upper section;
    a collector attached to said lower section for receiving solids from said container;
    a rotor rotatably mounted within said upper section;
    said lower section being of a truncoconical shape with its larger end directly attached to said upper section, and its smaller end being connected to said collector;
    a conduit having two ends, one of said conduit ends being arranged axially to the lower truncoconical section and adjacent the larger end of said lower section, the other of said conduit ends being connected to said outlet hole;
    a tap connected to said outlet hole, said tap selectively blocking said outlet hole when in a closed position according to the material level in said separator chamber, said upper section being connected to said outlet hole only through said conduit, said rotor causing substantially only liquid to be discharged through said conduit and said outlet hole when said tap is in an open position.

2. A separator as in claim 1, further comprising a spiral formed in an internal wall of said upper section, said spiral being positioned adjacent said rotor.

3. A separator as in claim 1, further comprising a stop rigidly mounted in said collector and rigidly mounted to said smaller end of said lower section, said stop having a plurality of radial slits for allowing passage of solids therethrough.

4. A separator as in claim 1, wherein said conduit has a spiral channel for the passage of liquid therethrough.

* * * * *